Figure 1:
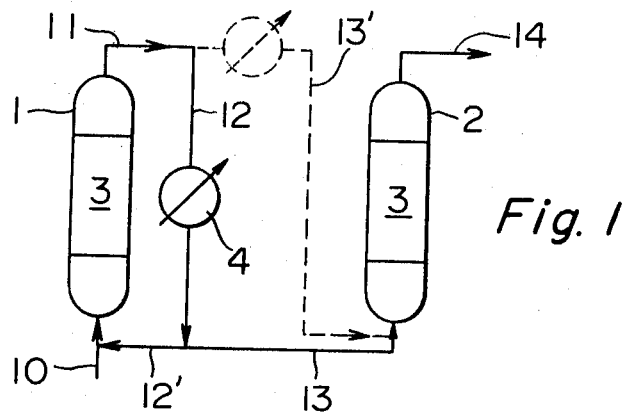

United States Patent [19]

Tokashiki et al.

[11] 3,997,616
[45] Dec. 14, 1976

[54] PROCESS FOR THE PREPARATION OF ALKYLTERALINS

[75] Inventors: Michiyuki Tokashiki, Tokuyama; Hiroshi Sakai, Iwakuni, both of Japan

[73] Assignee: Teijin Limited, Osaka, Japan

[22] Filed: June 27, 1975

[21] Appl. No.: 591,247

[52] U.S. Cl. .................... 260/666 PY; 260/668 F
[51] Int. Cl.$^2$ ........................................ C07C 13/28
[58] Field of Search ................. 260/666 PY, 668 F

[56] References Cited
UNITED STATES PATENTS 3,843,737  10/1974  Chong .................... 260/668 F

*Primary Examiner* — Veronica O'Keefe
*Attorney, Agent, or Firm* — J. Edward Hess; Donald R. Johnson; Stanford M. Back

[57] ABSTRACT

A process for the preparation of alkyltetralins which comprises feeding an alkenylbenzene into a reaction zone continuing a fixed bed of an acidic cyclization catalyst, and cyclizing it in the liquid phase at a temperature not higher than about 300° C., characterized in that:

i. at least a part of the reaction mixture containing the unreacted alkenylbenzene, which has been withdrawn from said reaction zone and in which the conversion of alkenylbenzene is below the intended final conversion, is cooled, and at least a part of the cooled reaction product in an amount sufficient to adjust the temperature of the reaction zone to not higher than about 300° C. is recycled to said reaction zone, and ii. the remainder of the reaction product is led into another reaction zone containing a fixed bed of acidic cyclization catalyst, and without the aforesaid recycling, further cyclized in the liquid phase until the intended final conversion is attained.

4 Claims, 4 Drawing Figures

PROCESS FOR THE PREPARATION OF ALKYLTERALINS

This invention relates to an improved process for the preparation of high purity alkyltetralins in excellent yields using inexpensive and compact apparatuses of simple construction by simple and easily controllable operations, while conveniently inhibiting objectionable side-reactions.

It is known that alkyltetralins are convertible to the corresponding alkylnaphthalenes upon dehydrogenation. Alkylnaphthalenes are useful as heat transfer media as they are, and also are valuable starting materials for various organic compounds. For example, alkylnaphthalenes are convertible to naphthoic acid, or naphthalenedicarboxylic acids, upon oxidation. Particularly dimethylnaphthalenes, for example, 2,6-,2,7-, 1,5-, and 1,4-dimethylnaphthalenes, are useful for making polyesters of favorable properties.

One of the pending problems in the preparation of such polyesters from dimethylnaphthalenes resides in the insufficient supply of high purity dimethylnapthalenes. For instance, 2,6-dimethylnaphthalene is present in petroleum fractions, but in very minor amounts and together with many other dimethylnaphthalene isomers. Because the 2,6-isomers possess physical properties closely resembling those of 2,6-dimethylnaphthalene and of some other isomers, it is extremely difficult to isolate the resulting 2,6-dimethylnapthalene. Both 2,6-, and 2,7-dimethylnaphthalenes, for example, have a boiling point of 262° C.

For this reason it has been desired to develop a process for preparing alkyltetralins by liquid phase cyclization of alkenylbenzenes in a reaction zone provided with a fixed bed of an acidic cyclization catalyst at a temperature not higher than about 300° C., which can form the desired product of high purity without forming difficulty separable by product isomers in any substantial amount.

As is well known, the above cyclization reaction in highly exothermic, and it is necessary therefore to control the thermal energy with industrial advantage. Hence, it can be easily anticipated that the reaction would be conveniently performed in heat exchanger type multitube reactors. On the other hand, a liquid-phase reaction system can avoid the operational and equipmental disadvantages suffered by vaporization of the starting material and liquefaction of the product which are required for vapor phase reaction system. The former furthermore can avoid the waste of thermal energy necessary in the latter system for the heating for vaporization and cooling for liquefaction. For these reasons it is expected that the above cyclization reaction would be advantageously performed in the multitube reactor in liquid phase.

Surprisingly, however, it is now discovered against the above expectation that the utilization of a heat exchanger type multitube reactor is disadvantageous for the liquid phase cyclization reaction of alkenylbenzene in the reaction zone having a fixed bed of the acidic cyclization catalyst. One of the drawbacks is that the reactor is required to have very complicated construction and hence, is expensive. This is because the specified type of the reactor contains a large number of relatively fine gauge tubes, each filled with the catalyst, and the reaction is effected as the liquid feed passes through said fine gauge tubes. The interspaces of the tubes are filed with a cooling medium to absorb the reaction heat. The linear velocity of the liquid flowing through the narrow reaction zone in the fine gauge tube with the fixed catalyst bed is rather low, and consequently, the rate of heat transfer by thermal convection is also rather low. In order to increase the rate of heat transfer, it is necessary to use the multitube reactor having a relatively large heat transfer area, that is, the reactor containing a larger number of the tubes of finer diameter.

Furthermore, hot spots are apt to be formed in a multitube reactor, which markedly promote the objectionable side-reactions in the cyclization reaction on the fixed catalyst bed intended by the present invention. For example, if 5-(o-tolyl)-2-pentene is used as the starting alkenylbenzene, objectionable side-reactions inevitably take place which include, for example, rearrangement of methyl groups of the object dimethyltetralin formed, and formation of dimers or by-products consisting of more monomer units as a result of linking of side-chain double bond of said 5-(o-tolyl)-2-pentene with the benzene ring in other 5-(o-tolyl)-2-pentene and/or the benzene ring of object dimethyltetralin. Again, when the temperature of hot spots is extremely high, there is a possibility that even cracking of the starting 5-(o-tolyl)-2-pentene may be caused.

A still another drawback is that, because the reaction is effected on the fixed bed of acidic cyclization catalyst, in other words, effected in the liquid phase using solid catalyst, the solid catalyst tends to be softened and/or swollen, if different in degrees for individual catalysts. This tendency is particularly remarkable with solid phosphoric acid catalyst which is a specially preferred catalyst for the intended reaction. This phenomenon makes the withdrawal of the waste catalyst from the multitube reactor extremely cumbersome and difficult, and furthermore reduces the void ratio in the fixed catalyst bed to impede the passage of feed liquid and/or to make the liquid flow non-uniform. In an extreme case, a drastic variation in the liquid flow rate occurs among the many tubes, rendering the reaction inoperable.

It has therefore been found to be entirely unrecommendable to practice the specified liquid phase cyclization reaction in a heat exchanger type multitube reactor which has been expected to be most suitable for this invention.

Accordingly, we pursued out studies on the utilization of non-heat exchanger type reactor. It is known to effect the reaction in the reaction zone provided with a non-heat exchanger type reactor, in which a part of the reaction product withdrawn from the reaction zone having a fixed bed of an acidic cyclization catalyst is cooled and recycled into the reaction zone (U.S. Pat. No. 3,843,737). Such a system may effectively overcome a number of drawbacks inherent in the utilization of above heat exchanger type reactor, but it is found difficult to practice the liquid phase cyclization reaction of alkenylbenzenes on fixed catalyst bed system with industrial advantage, by the adoption of said method alone.

One reason for the difficulty is that, in the reaction in the non-heat exchanger type reactor in which a part of the reaction product is cooled and recycled into the substantially heat insulated reaction zone, a considerably large amount of the cooled recycling liquid is required for desirable controlling of the reaction temperature. For example, the cooled reaction product must be recycled in an amount of preferably approximately ten times, normally about five to twenty times, the volume of the fresh alkenylbenzene supplied to the reaction zone. This means that the fresh alkenylbenzene supply is greatly diluted with the reaction product being recycled, when fed into the reaction zone. On the other hand, it is a chemical common sense that the reaction should be effected to obtain the object product in high conversion to render the process economically acceptable, for example, the highest possible conversion, normally not lower than 95%. This is particularly true with the reaction intended by the present invention, in which the physical properties of the starting alkenylbenzene, object product, and the by products resemble closely and their separating procedures are highly expensive. Thus, the above system has the drawbacks in that the alkenylbenzene concentration in the reaction zone inevitably becomes considerably low, and an increased amount of the solid catalyst is required. Furthermore, because of the required recycling of considerably large amount of the cooled reaction product and use of increased amount of the catalyst, the object alkyltetraline comes into contact with the catalyst at a considerably high concentration for an increased length of time, which unavoidably results in the increase of objectionable side-reaction, i.e., the rearrangement reaction of methyl groups in the alkyltetralin. Again, with the increase in the amounts of catalyst and the reaction product to be recycled, as the logical consequence the size of the apparatus must also be disadvantageously enlarged.

We have extensively worked for finding solutions to the technical problems arising anew with the temperature-controlling system in the exothermic reaction by recycling the cooled current of reaction product, which is admittedly useful for overcoming the disadvantages of using a heat exchanger type reaction zone. As a result we discovered that a markedly improved cyclization reaction can be performed by not effecting the reaction to the desired final conversion in a single reaction zone, but carrying out the first-stage reaction to a conversion lower than the final conversion under the reaction temperature-controlling system by recycling the cooled reaction product, and introducing the lower conversion product into another reaction zone and effecting the second-stage reaction there until the desired final conversion is obrained, and without the aforesaid recycling. For example, if the intended final conversion of alkenylbenzene is approximately 99.5% it is possible to appreciable reduce the amount of the reaction product recycled in the first-stage reaction, using the catalyst in an amount as small as approximately one-fourth of that required in the prior art, while conveniently inhibiting the objectionable side-reactions, and to obtain the high purity object alkyltetralin with an excellent one-pass yield of as high as approximately 92%. Furthermore, the liquid phase catalytic cyclization reaction of alkenylbenzene can be practiced with remarkable industrial advantage, using non-expensive apparatuses of simple construction.

Accordingly, an object of the present invention is to provide a process for making high purity object alkyltetralins in excellent yields, using a cheap and compact apparatus of simple construction, by simple and easily controllable operations, while conveniently inhibiting the objectionable side-reactions.

Still many other objects and advantages of the invention will become apparent from the following description.

According to the subject invention, in the preparation of alkyltetralins by feeding an alkenylbenzene of the formula,

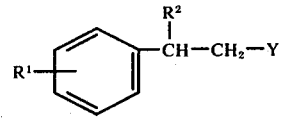

in which $R^1$ is a member of the group consisting of hydrogen, methyl and ethyl, $R^2$ is hydrogen or methyl, $R^1$ and $R^2$ are same or different, and Y represents $-CH=CH-CH_3$ or $-CH_2-CH=CH_2$ group, into a reaction zone containing a fixed bed of an acidic cyclization catalyst, and cyclizing it in the liquid phase at a temperature not higher than about 300° C., i. at least a part of the reaction mixture containing the unreacted alkenylbenzene, which has been withdrawn from said reaction zone and in which the conversion of alkenylbenzene is below the intended final conversion, preferably that below approximately 95%, is cooled and at least a part of the cooled reaction product is recycled to said reaction zone, the amount of the rcycled reaction product being sufficient to adjust the temperature of the reaction zone to not higher than approximately 300° C., and ii. the remainder of the reaction product is introduced to another reaction zone containing a fixed bed of acidic cyclization catalyst and without the aforesaid recycling, further reacted until the intended final conversion is attained.

The above-described liquid phase catalytic cyclization reaction can be schematically shown below, taking up an example of the preparation of 1,5-dimethyltetralin from 5-(o-tolyl)-2-pentene.

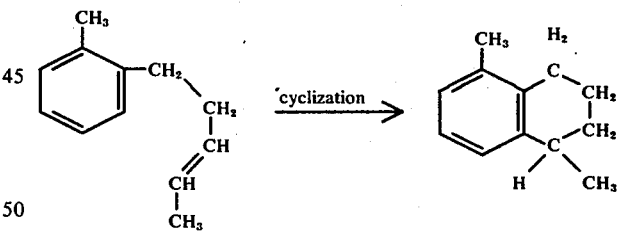

In the above reaction, a rearrangement reaction of methyl groups in the once formed 1,5-dimethyltetralin is apt to take place, and, for example, there occur such by products which cause the undesirable formation of 2,7-dimethylnaphthalene in the preparation of 2,6-dimethylnaphthalene by dehydrogenating dimethyltetralin are isomerizing the resulting dimethyl naphthalene. The presence of such a by product in the reaction mixture even in a very minor amount markedly reduces the commercial value of the final product.

For example, in the preparation of 2,6-dimethylnaphthalene, 1,5-dimethylnaphthalene, 1,6-dimethylnaphthalene, and 2,6-dimethylnaphthalene (the three isomers may be hereinafter referred to as 2,6-family-DMN) are mutually isomerized, but seldom isomerized to 1.7-dimethylnaphthalene, 1.8-dimethylnaphthalene, and 2,7-dimethylnaphthalene (which hereinafter may be referred to as 2,7-family-DMN). Conversely, 2,7-family-DMN show isomerization within their family, but are seldom isomerized to 2,6-family-DMN. For this reason, 1,6-dimethyltetralin and 2,6-dimethyltetralin which form the DMN belonging to the same family with that formed from 1,5-dimethyltetralin may be formed as a by-product during the 1,5-dimethyltetralin forming reaction from 5-(o-tolyl)-2-pentene with no detrimental effect, but the formation of by-product 1,7-dimethyltetralin, 1,8-dimethyltetralin, and 2,7-dimethyltetralin which form the 2,7-family-DMN is seriously deterimental to the 2,6-dimethylnaphthalene isomerization reaction step.

One disadvantageous aspect of such by product formation is that, because 2,6-dimethylnaphthalene and 2,7-dimethylnaphthalene possess nearly the same boiling point and form eutectic crystal, it is extremely difficult to separate the two at the economically justifiable expense. Thus, there is no positively effective means for removing the 2,7-family-DMN in the dimethylnaphthalene isomerization process (inclusive of the crystallization process of 2,6-dimethylnaphthalene), but it is hoped that the 2,7-family-DMN would be decomposed by the disproportionation reaction and the like which are presumed to occur simultaneously with the isomerization of 2,6-family-DMN, or the 2,7-family-DMN may be discharged from the isomerization procedure as the impurities in the product 2,6-dimethylnaphthalene. Therefore, it is desirable to keep the 2,7-family-DMN in the feed to the isomerization recycle process to the possible minimum. Furthermore, in the dimethylnaphthalene isomerization reaction, the unconverted material is recirculated and re-used to improve the yield, and hence, when the 2,7-family-DMN content in the system becomes high, the required amount of recycle material increases accordingly, which results in the higher plant-construction cost and use of more utilities. The increasing ratio of the recycle material differs somewhat depending on the isomerization conditions, but in typical cases the increase of 2,7-family-DMN in the feed to the isomerization recycle zone by 1 weight percent invites that of the reacryle liquid by approximately 40 weight percent, the isomerization catalyst being hydrogen-type mordenite.

According to the present invention, the formation of such objectionable by products can be conveniently inhibited.

Any of the known acidic cyclization catalysts conventionally used in the liquid phase catalytic cyclization reaction may be used in this invention, the preferred examples of such solid catalyst including solid phosphoric acid, boron phosphate, partly or entirely hydrogen-type mordenite, partly metal-exchanged or contained hydrogen-type mordenite and silica-alumina. Solid phosphoric acid is particularly preferred for the practice of this invention. The grain size of the catalyst ranges preferably from 0.5 mm to 50 mm, particularly from 1 mm to 10 mm. The fixed catalyst bed may be provided on multi-stages or single stage.

In order to make the description more easily understandable, the unique features of the subject process will be hereinafter more specifically illurtrated, referring to the attached drawings.

FIG. 1 shows one embodiment suited for practising the subject process by a simplified flow chart. Referring to FIG. 1, the fresh starting material alkenylbenzene is fed into the first reaction zone 1 containing a fixed bed 3 of an acidic cyclization catalyst through path 10. The reaction product containing some unreacted alkenylbenzene, of which conversion is lower than the intended final conversion, is withdrawn from the reaction zone 1, and led through the paths 11 and 12. During the travelling, at least a part of said reaction product is cooled by the cooling means provided at a suitable spot or spots of said paths, for example, a heat exchanger 4. The cooling means itself is not critical, but any known cooling means can be suitably utilized, for example, multitube heat exchanger, air fin cooler, plate heat exchanger, and the like. In the embodiment of FIG. 1, the whole reaction product is cooled, and a part thereof is led through the path 12', and joined by the new feed flow from the path 10 to be recycled to the reaction zone 1, the rest being sent to the second reaction zone 2 through path 13. As indicated by a dotted line in FIG. 1, a part of the reaction product may be cooled and recycled through the paths 12 and 12', and the rest, cooled separately and led into the second reaction zone 2 through path 13'.

The temperature of the reaction product to be recycled can be suitably determined, so far as it is sufficiently low to allow the product to absorb the reaction heat in the first reaction zone. The recycle flow is preferably cooled to the temperature lower than that at the exit of the first reaction zone by about 5°–40° C. The flow rate of the recycle liquid should be one sufficient to adjust the temperature of the first reaction zone to no higher than about 300° C., preferably about 150°–270° C., especially about 160°–250° C. The amount of the recycle liquid (by volume) normally ranges from about 1 to about 50, preferably about 2–30, particularly about 4–25, when expressed by the recycle ratio (volume of the reaction product to be recycled per unit time volume of freshly fed starting material per unit time).

The reaction is effected at a temperature not higher than about 300° C., preferably not lower than about 100° C., particularly at about 150°–270° C., above all, about 160°–250° C. The reaction pressure normally ranges from the normal to about 25 atmospheres, or even higher if desired. In any case, it should be sufficient to allow the reaction at the liquid phase.

According to the invention, the reaction in the first reaction zone is effected to a conversion lower than that finally intended. The final conversion being normally about 95–100% as already mentioned, the conversion in the first reaction zone is normally kept no higher than about 95%. If a lower final conversion is intended, obviously the conversion in the first reaction zone can be lowered accordingly. Normally it is convenient to adopt the conversion lower than that finally intended by about 2–30%, in the first reaction zone.

Figures 1, 2:
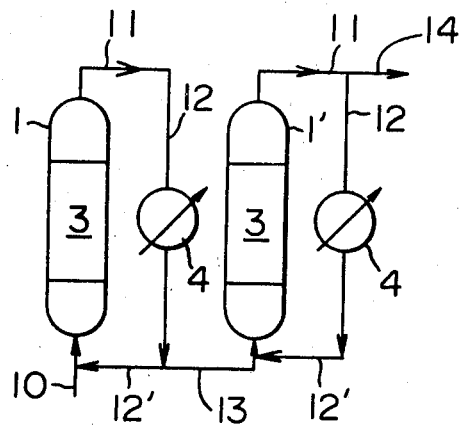
Figure 2:
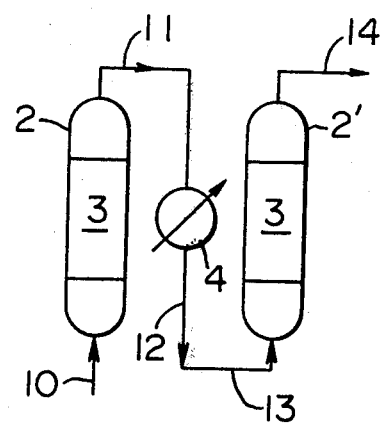

According to the invention, the reaction effected under the temperature control by recycling a part of the cooled reaction product of low conversion may be carried out in plural reaction zones as illustrated, for example, in FIG. 2-1, instead of the single reaction zone shown in FIG. 1. The rest of the reaction product from the reaction zone 1 is led to another reaction zone 2 containing a fixed bed 3 of an acidic cyclization catalyst, as shown in FIG. 1. In the second reaction zone 2, the liquid phase catalytic reaction is further advanced until the intended final conversion is attained, without recycling as practised in the reaction zone 1. This advanced reaction again can be effected in plural reaction zones as shown, for example, in FIG. 2-2. Referring again to FIG. 1, the flow of the reaction product leaving the second reaction zone 2 is led through path 14 and withdrawn, which may be further subjected to separation, purification or reaction procedures known per se, if necessary.

As above-described, according to the subject process, at least a part of the reaction product containing unreacted alkenylbenzene which is withdrawn from the first reaction zone 1 at a conversion lower than that finally intended, is cooled, and at least a part of the cooled reaction product is recycled to the reaction zone 1 in an amount sufficient to adjust the temperature of the first reaction zone to not higher than about 300° C. The rest of the low conversion reaction product is led into another reaction zone 2, where the liquid phase cyclization reaction is continued until the intended final conversion is obtained, without the recycling as effected in the reaction zone 1. The catalyst, reaction temperature and pressure in the reaction zone 2 can be suitably selected similarly to those for the reaction zone 1.

Figures 2, 3:
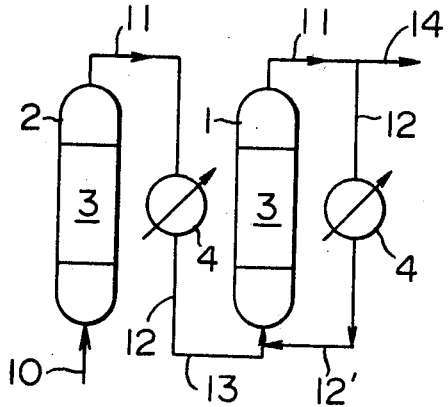

If the second reaction zone 2 is omitted but two first reaction zones ( 1,1' as indicated in FIG. 2-1) are provided (Control A); or the first reaction zone 1 is omitted but two second reaction zones 2,2' are provided (Control B), the advantages of the present invention cannot be achieved. Or, the advantages of the invention are again lost if the order of the reaction zones 1 and 2 is reversed as shown in FIG. 2-3 (Control C). The object of this invention neither can be achieved by the single first reaction zone 1 alone (Control A') or the single second reaction zone 2 alone (Control B').

The results of the experiments for making 1,5-dimethyltetraline from 5-(o-tolyl)-2-pentene with the final conversion of about 99.5%, which were run using identical fixed beds of solid phosphoric acid, in the manner according to the subject process and the above-described Controls A, A', B, B' and C, under a certain set of reaction conditions are shown in Table 1, in which the definitions of the given items are as follows:

1. Yield yield (%)= $W_1 + W_2$ in which $W_1$ is the weight percent of 1,5-dimethyltetralin in the final reaction product, and
$W_2$ is the weight percent of 1,6-dimethyltetralin in the final reaction product.

2. Effective selectivity

In the reaction, besides the object 1,5-dimethyltetralin, such by-products as 1,6-dimethyltetralin, 1,7-dimethyltetralin, 1,8-dimethyltetralin, 5-(o-tolyl) -3-pentene, 5-(o-tolyl)-4-pentene, and high-boiling by-products (the boiling points not lower than 140° C. at 5 mmHg) are formed. Of these by-products, 1,6-dimethyltetralin is convertible, similarly to 1,5-dimethyltetralin, to useful 2,6-dimethylfaphthalene upon dehydrogenation and isomerization. Therefore, the "effective selectivity" signified the selectivity (%) based on the sum of the 1,5- and 1,6-dimethyltetralins formed.

Effective selectivity (%) = $\frac{W_1 + W_2}{100 - W_3} \times 100$ in which $W_1$ is the weight percent of 1,5-dimethyltetralin in the final reaction product,
$W_2$ is the weight percent of 1,6-dimethyltetralin in the final reaction product and
$W_3$ is the weight percent of 5-(o-tolyl)-2-pentene in the final reaction product, 3. Amount of by products The total sum of the 1,7-, 1,8-, and 2,7-dimethyltetralins, which cause the formation of undesirable 2,7-dimethylnaphthalene during the conversion of object alkyltetralin to 2,6-dimethylnaphthalene as above-described, is shown as the content (% by weight) thereof in the final reaction product.

4. Required amount of the catalyst

The amount of catalyst required for each run is shown by index number, with that for the subject process being set to be 100.

5. Recycle ratio is the isomerization recirculation system

In the process for making 2,6-dimethylnaphthalene through isomerization step (inclusive of crystallization step) of the dimethylnaphthalene resulting from the dehydrogenation of cyclization product of 5-(o-tolyl)-2-pentene, the filtrate remaining after the removal of crystallized 2,6-dimethylnaphthalene is recirculated into the entrance of isomerization reaction zone. The quantitative ratio is such a recycle system is indicated by the index number based on the recycled amount of the reaction product in the present invention as 100. In the runs, hydrogen-type mordenite is used as the isomerization catalyst.

Table 1

|  |  | Subject process | Control A | Control A' | Control B | Control B' | Control C |
|---|---|---|---|---|---|---|---|
| (1) | Yield (%) | 91.5 | 89.0 | 88.0 | 65.0 | 47.5 | 84.0 |
| (2) | Effective selectivity (%) | 92.0 | 89.4 | 88.4 | 65.3 | 47.7 | 84.4 |
| (3) | Amount of by-product | 1.0 | 1.4 | 1.7 | 3.5 | 6.5 | 2.3 |
| (4) | Catalyst required | 100 | 104 | 376 | 29 | 14 | 463 |
| (5) | Recycle ratio in isomerization recirculation system | 100 | 113 | 124 | 212 | 440 | 148 |

"Solid phosphoric acid" useful as the catalyst in this invention means the catalyst, as well known, composed chiefly of phosphoric acid carried on silica or aluminosilicate. As the phosphoric acid, ortho-, pyro- and polyphosphoric acids such as tri-, tetra- and hexa-phosphoric acids and mixtures of the foregoing may be named. The preferred carriers of the phosphoric acid are provided, for example, by diatomaceous earth, celite, bentonite, silica, acidic clay and montmorillonite.

Such solid phosphoric acid catalyst can be prepared, for example, by mixing orthosphosphoric acid or a polymer thereof with a suitable amount of a carrier, and heat-treating the mixture. The heat treatment is normally performed at a temperature ranging about 150°–800° C.

It is also permissible to add to the solid phosphoric acid catalyst, a minor amount of a third component such as an oxide or phosphate of nickel, copper, and the like; ammonium phosphate, an alkali metal salt of phosphoric acid; sulfuric acid, ammonium sulfate, aluminium sulfate and the like.

The phosphoric acid content of the solid phosphoric acid catalyst can be indicated in terms of phosphorus pentoxide ($P_2O_5$) content of said catalyst. while there is no critical limitation on the phosphorus pentoxide content, normally that of about 10 – 90% by weight, particularly about 30–70% by weight, is preferred.

The boron phosphate catalyst can be formed by mixing boric acid and orthophosphoric acid, and reacting the mixture at 60° – 100° C. The boron phosphate catalyst of high activity is obtained particularly when 1–1.5 mols of orthophosphoric acid is used per mol of boric acid. Other known methods for making the catalyst involves heating of a mixture of boron oxide with phosphorus oxychloride and heating of a mixture of boron trichloride and phosphorus pentoxide. The boron phosphate catalyst obtained is dried in vacuo at room temperature to 200° C. (Concerning the means for making boron phosphate catalyst, see J. W. Meller, *A Comprehensive Treatise On Inorganic And Theoretical Chemistry*, Vol. 5, if necessary).

The boron phosphate catalyst so prepared may be used as it is if already dried, or may be first calcined at the temperatures up to 1000° C. Particularly those calcined at 200° – 600° C. provide favorable catalysts.

The boron phosphate catalyst may be used concurrently with an other cyclization catalyst, e.g., solid phosphoric acid, or may be supported on inert carriers, e.g., alumina. Furthermore, it may be used in the concurrent presence of metal salt of inorganic acid such as nickel sulfate, aluminium sulfate or aluminum phosphate, or metal oxides such as the oxides of zinc, titanium, zirconium, cobalt, and the like.

As the hydrogen-type mordenite catalyst, those having the pore size of about 7–10 A or greater diameters, i.e., the mordenite having large ports are preferred. Such preferred mordenite can be either artificially synthesized or obtained by treating natural mordenite of finer pore size with hydrochloric acid. It is preferred that not less than 50%, particlarly not less than 80%, of the total ion-exchangeable cations in the hydrogen-type mordenite should be hydrogen ion.

The hydrogen-type mordenite catalyst may be used by itself, or concurrently with suitable promotor and/or carrier. As the useful promotions and/or carriers, for example, natural aluminosilicate such as bentonite and acidic clay, silica, alumina, silica-alumina and sy synthetic zeolite can be named.

In order to prolong the catalyst life in the liquid phase cyclization reaction in the presence of solid phosphoric acid catalyst and boron phosphate catalyst, it is preferred to cause the concurrent presence of a fixed amount of water in the reaction liquid. The preferred water content ranges from about 10–2,000 ppm, particularly from about 100 – 1,000 ppm.

The solid phosphoric acid catalyst, however, exhibits strongly corrosive property in the presence of water at the liquid phase cyclization reaction temperatures, when ordinary carbon steel or SUS 304 stainless steel is used as the construction material of the reactor, making the continuation of said liquid-phase cyclization reaction over a long period difficult. The corrosion of reactor also poses a safety problem. In that case, copper and/or alloys containing no less than 1 wt % of copper can be used as the construction material of the reactor which contacts the solid phosphoric acid catalyst, effectively overcoming the above drawbacks.

Examples of the alkenylbenezenes expressed by the general formula given in the earlier part of this specification, which are useful as the starting material of the subject process, include the following: 5-phenyl-2-pentene, 5-(o-tolyl)-2-pentene, 5-(p-tolyl)-2-pentene, 5-(m-tolyl)-2-pentene, 5-phenyl-1-pentene, 5-(o-tolyl)-1-pentene, 5-(p-tolyl)-1-pentene, 5-(m-tolyl)-pentene, 5-methyl-5-phenyl-2-pentene. 5-methyl-5-phenyl-1-pentene, 5-methyl-5-(o-ethylphenyl)-2-pentene, 5-methyl-5-(o-ethylphenyl)-1-pentene, 5-methyl-5-(p-tolyl)-2-pentene, 6-(o-tolyl)-3-hexene, 6-(o-tolyl)-2-hexene, 6-methyl-6-phenyl-3-hexene, 6-methyl-6-phenyl-2-hexene and 6-phenyl-3-hexene.

Upon cyclization of such alkenylbenzenes the corresponding alkyltetralins are obtained, for example, 1-methyltetralin from 5-phenyl-2-pentene, 1,5-dimethyltetralin from 5-(o-tolyl)-2-pentene, 1,7-dimethyltetraline from 5-(o-tolyl)-z-pentene, 1,6-dimethyltetralin and 1,8-dimethyltetralin from 5-(m-tolyl)-2-pentene, 1-methyltetralin from 5-phenyl-1-pentene, 1,4-dimethyl-tetralin from 5-methyl-5-phenyl-2-pentene, and 5-methyl-1-ethyltetralin from 6-(o-tolyl)-3-hexene.

Hereinafter the invention will be more specifically illustrated with reference to several embodiments for practicing the subject process.

EXAMPLE 1

The process of the invention was practiced in accordance with the flow chart of FIG. 1. A 340 - cm high columnar reactor of 65.9 mm inner diameter was filled with 7.8 kg of solid phosphoric acid catalyst (N501 manufactured by Nikki Kagaku Co., Japan, in the form of 6 mm $\phi$ × 6 mm cylinders), to serve as the first stage reaction zone 1. The height of the catalyst bed was 284 cm. Also a 760-cm high columnar reactor of 27.4 mm inner diameter was filled with 4.05 Kg of the same solid phosphoric acid catalyst, to serve as the second stage reaction zone 2. The height of the catalyst bed was 715 cm.

As the starting alkenylbenzene, 99.8% pure 5-(o-tolyl)-2-pentene was used. The liquid phase catalytic cyclization was run under the conditions specified in Table 2 below, with the results as given in the same table.

Table 2

| | | |
|---|---|---|
| Introducing temperature of mixture of strating material and recirculation flow into reaction zone 1 (temperature at the entrance, ° C.) | | 180 |
| Temperature of reaction product withdrawn from reaction zone 1 (temperature at the exit, ° C.) | | 200 |
| Introducing temp. of the reaction product into reaction zone 2 (temperature at the entrance, ° C.) | | 180 |
| Temperature of product with intended final conversion withdrawn from reaction zone 2 (temperature at the exit, ° C.) | | 215 |
| Space velocity of liquid per 1 Kg of catalyst (Kg/hr.) | reaction zone 1 | 0.46 |
| | reaction zone 2 | 0.89 |
| | zone 1 + | |

Table 2-continued

| | |
|---|---|
| zone 2 | 0.32 |
| Recycling ratio in reaction zone 1 | 15.5 |
| Alkenylbenzene conversion in reaction product from reaction zone 1 (%) | 90.1 |
| Final alkenylbenzene conversion in reaction product from reaction zone 2 (%) | 99.5 |
| (1) yield (%) | 91.5 |
| (2) Effective selectivity (%) | 91.9 |
| (3) Amount of by-product (wt.%) | 1.0 |

EXAMPLE 2

Example 1 was repeated except that the amount of the catalyst filling the first reaction zone 1 was reduced to 5.85 Kg, and the second reaction zone 2 was divided into two to enable the repetition of step (ii) twice. That is, a partition sheld was provided within the catalyst bed in the second stage reaction zone 2 to form two completely separated areas between which no mixing of the fed liquid could occur. The liquid which left the catalyst bed on the lower shelf was cooled to 180° C. with a cooler, and thereafter led into the lower part of the catalyst bed on the upper shelf. The conditions of the liquid phase catalytic cyclization reaction and the results were as shown in Table 3 below.

Table 3

| | | |
|---|---|---|
| Introducing temperature of mixture of starting material and recirculation flow into reation zone 1 (temperature at the entrance, ° C.) | | 180 |
| Temperature of reaction product withdrawn from reaction zone 1 (temperature at the exit, ° C.) | | 200 |
| Introducing temperature of the reaction product into lower shelf of reaction zone 2 (temperature at the entrance, ° C.) | | 180 |
| Temperature of the reaction product withdrawn from lower shelf of reaction zone 2 (temperature at the exit, ° C.) | | 200 |
| Introducing temperature of the reaction product into upper shelf of reaction zone 2 (temperature at the entrance, ° C.) | | 180 |
| Temperature of the product with intended final conversion withdrawn from upper shelf of reaction zone 2 (temperature at the exit, ° C.) | | 200 |
| Space velocity of liquid per 1 kg of catalyst (kg/hr.) | Reaction zone 1 | 0.53 |
| | Reaction zone 2 lower shelf | 4.71 |
| | Reaction zone 2 upper shelf | 0.92 |
| | Zone 1 + lower shelf of zone 2 + upper shelf of Zone 2 | 0.32 |
| Recyling ratio in reaction zone 1 | | 15.2 |
| Alkenylbenzene conversion in reaction product from reaction zone 1 (%) | | 88.6 |
| Alkenylbenzene conversion in reaction product from lower shelf of reaction zone 2 (%) | | 94.0 |
| Alkenylbenzene conversion in reaction product from upper shelf of reaction zone 2(%) | | 99.5 |
| (1) Yield (%) | | 92.3 |
| (2) Effective selectivity (%) | | 92.5 |
| (3) Amount of by-products (wt.%) | | 0.9 |

CONTROL 1

The liquid phase catalytic cyclization reaction 5-(o-tolyl)-2-pentene was performed similarly to Example 1, except that the second reaction zone 2 was omitted, and a part of the reaction product flow withdrawn from the first reaction zone 1 was cooled and recirculated, while the rest was withdrawn as it was, without being cooled, the final conversion at the reaction zone 1 being 99.5%. The reaction conditions and the results were as shown in Table 4 below.

Table 4

| | |
|---|---|
| Introducing temperature of mixture of starting material and recirculation flow into reaction zone 1 (temperature at the entrance, ° C.) | 180 |
| Temperature of reaction product withdrawn from reaction zone 1 (temperature at the exit, ° C.) | 215 |
| Space velocity of liquid per 1 Kg of catalyst (Kg/Hr.) | 0.085 |
| Recycling ratio in reaction zone | 9.4 |
| Final conversion (%) | 99.5 |
| (1) Yield (%) | 88.0 |
| (2) Effective selectivity (%) | 87.3 |
| (3) Amount of by-products (wt.%) | 1.7 |

The results shown in above Table 4 indicates that Control 1 requires markedly lower space velocity than that in Example 1, and shows very low effective selectivity. The low space velocity means that a larger amount of catalyst is necessary for the production of same amount of object product, i.e., low productive efficiency.

CONTROL 2

In the practices of Example 1, the second reaction zone 2 was omitted, the amount of the catalyst froming a fixed bed in the reaction zone 1 was reduced to 1 Kg, and no recirculation of the cooled reaction product withdrawn from the reaction zone 1 was effected. The reaction was run in the manner to make the final conversion in the reaction zone 1, 99.5%. Because the temperature in the vicinity of exit from reaction zone 1 became extremely high due to the reaction heat, the reaction was effected under an elevated pressure of 100 kg/cm²·gauge in order to maintain the system at liquid phase. The reaction, conditions and the results were as shown in Table 5 below.

Table 5

| | |
|---|---|
| Introducing temperature of starting material into reaction zone 1 (temperature at the entrance, ° C.) | 180 |
| Temperature of reaction product withdrawn from reaction zone 1 (temperature at the exit, ° C.) | 546 |
| Space velocity of liquid per 1 Kg of catalyst (Kg/hr.) | 2.4 |
| Final conversion (%) | >99.5 |
| (1) Yield (%) | 47.5 |
| (2) Effective selectivity (%) | 47.7 |
| (3) Amount of byproducts (wt.%) | 6.5 |

We claim:

1. A process for the preparation of alkyltetralins which comprises feeding an alkenylbenzene of the formula

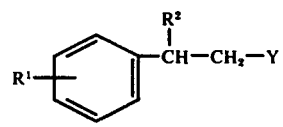

in which $R^1$ is a member of the group consisting of a hydrogen atom, and methyl and ethyl groups, $R^2$ is a hydrogen atom or methyl group, $R^1$ and $R^2$ are the same or different and Y represents $-CH=\lambda CH-CH_3$ or $-CH_2-CH=CH_2$, into a reaction zone contining a fixed bed of an acidic cyclization catalyst, and cyclizing it in the liquid phase at a temperature not higher than about 300° C., characterized in that:

i. at least a part of the reaction mixture containing the unreacted alkenylbenzene, which has been withdrawn from said reaction zone and in which the conversion of alkenylbenzene is below the intended final conversion, is cooled, and at least a part of the cooled reaction product in an amount sufficient to adjust the temperature of the reaction zone to not higher than about 300° C. is recycled to said reaction zone, and ii. the remainder of the reaction product is led into another reaction zone containing a fixed bed of acidic cyclization catalyst, and without the aforesaid recycling, further cyclized in the liquid phase until the intended final conversion is attained.

2. The process according to claim 1, in which the alkenylbenzene conversion in the reaction product withdrawn from the reaction zone in said step (i) is not higher than about 95%.

3. The process according to claim 1, in which the alkenylbenzene conversion in the reaction product withdrawn from the reaction zone in said step (i) is about 3 to 20% lower than the intended final conversion.

4. The process according to claim 1, in which the reaction is performed at a temperature within the range of about 150° to 270° C.

* * * * *